United States Patent [19]

Clubley et al.

[11] Patent Number: 4,847,017

[45] Date of Patent: Jul. 11, 1989

[54] HYDROXYPHOSPHONOCARBOXYLIC ACIDS

[75] Inventors: Brian G. Clubley, Wilmslow; David W. Cartmell, Blackrod; David C. Parker, Macclesfield, all of England

[73] Assignee: Ciga-Geigy Corporation, Ardsley, N.Y.

[21] Appl. No.: 67,524

[22] Filed: Jun. 29, 1987

[30] Foreign Application Priority Data

Jul. 5, 1986 [GB] United Kingdom ............... 8616447

[51] Int. Cl.$^4$ .............................................. C07F 9/02
[52] U.S. Cl. .................................................. 562/24
[58] Field of Search .................... 260/502.4 C

[56] References Cited

U.S. PATENT DOCUMENTS

| | | | |
|---|---|---|---|
| 3,032,500 | 5/1962 | Milks et al. | 252/8.5 |
| 3,719,598 | 3/1973 | King | 252/33.4 |
| 3,933,427 | 1/1976 | Bohnsack et al. | 252/389.23 |
| 4,042,324 | 8/1977 | Auel et al. | 252/389.23 |
| 4,052,160 | 10/1977 | Cook et al. | 252/389.23 |
| 4,057,511 | 11/1977 | Bohnsack et al. | 252/389.23 |
| 4,105,551 | 8/1978 | Smith et al. | 210/700 |
| 4,243,417 | 1/1981 | Grourke et al. | 106/14.13 |
| 4,351,796 | 9/1982 | Marshall | 106/14.13 |
| 4,468,355 | 8/1984 | Krause et al. | 260/502.4 C |
| 4,606,890 | 8/1986 | Fisk | 422/15 |
| 4,649,025 | 3/1987 | Hwa et al. | 252/389.23 |
| 4,689,200 | 8/1987 | Cook et al. | 252/389.23 |

FOREIGN PATENT DOCUMENTS

| | | |
|---|---|---|
| 2310450 | 9/1974 | Fed. Rep. of Germany . |
| 2658961 | 12/1976 | Fed. Rep. of Germany . |
| 0222597 | 12/1983 | Fed. Rep. of Germany . |
| 554024 | 6/1978 | Japan . |
| 1017115 | 2/1980 | Japan . |

OTHER PUBLICATIONS

Research Disclosures No. 18170 (May 1979).
Japanese Sho 55-2718 (abstract) 1980.

*Primary Examiner*—Paul Lieberman
*Assistant Examiner*—Willie J. Thompson
*Attorney, Agent, or Firm*—Luther A. R. Hall; JoAnn Villamizar

[57] ABSTRACT

New compounds have the formula I:

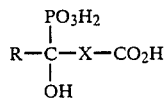

wherein R is a $C_1$-$C_{12}$ straight or branched chain alkyl residue, a $C_2$-$C_{12}$ straight or branched chain alkenyl residue, a $C_5$-$C_{12}$ cycloalkyl residue, a $C_6$-$C_{10}$ aryl residue or a $C_7$-$C_{12}$ aralkyl residue; and X is a $C_1$-$C_{10}$ straight or branched alkylene residue, a $C_2$-$C_{10}$ straight or branched chain alkenylene residue or a $C_6$-$C_{10}$ arylene residue; as well as derivatives of the compounds of formula I; and enantiomers, racemic mixtures, and mixtures of diastereomers.

The new compounds are useful e.g. as corrosion inhibitors in aqueous systems.

4 Claims, No Drawings

HYDROXYPHOSPHONOCARBOXYLIC ACIDS

The present invention relates to hydroxyphosphono carboxylic acids, to a process for their production and to their use e.g. as corrosion inhibitors.

In Japanese laid open Patent Application No. 80-29,883 there are described compounds having the formula:

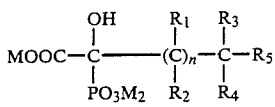

in which
$R_1$ is H or 1-3C alkyl;
$R_2$, $R_3$, $R_4$ and $R_5$ are each H, halogen, —COOM, $PO_3M_2$ or OH;
n is 0, 1, 2 or 3; and
M is H or a cation.

The compounds are said to be useful as components of developing solutions for light-sensitive silver halide colour photographic material, and to impart stability to those solutions, even when the solutions contain metal ion.

Moreover, in Research Disclosures No. 18170 (May 1979) which also relates to photographic processing solutions, amongst a long list of phophonocarboxylic acids said to be useful as chelating agents, there can be found 1-hydroxy-1-phosphono-ethane-2-carboxylic acid.

We have now found certain new hydroxyphosphono monocarboxylic acid derivatives which exhibit excellent corrosion inhibition behaviour in a wide variety of substrates.

The present invention provides compounds having the formula (I):

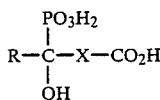

wherein R is a $C_1$–$C_{12}$ straight or branched chain alkyl residue, a $C_2$–$C_{12}$ straight or branched chain alkenyl residue, a $C_5$–$C_{12}$cycloalkyl residue, a $C_6$–$C_{10}$aryl residue or a $C_7$–$C_{12}$ aralkyl residue; and X is a $C_1$–$C_{10}$ straight or branched alkylene residue, a $C_2$–$C_{10}$ straight or branched chain alkenylene residue or a $C_6$–$C_{10}$arylene residue; as well as derivatives of the compounds of formula I.

By the term "derivatives" of the compounds of formula I, we mean salts formed by replacing one or more acidic hydrogen atoms by, e.g. an alkali metal, alkaline earth metal a transition metal, ammonium or an amine group, or partial esters. Other derivatives intended are the dehydration products corresponding to the compounds of formula I e.g. lactones having the formula:

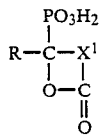

in which R has its previous significance and $X^1$ is —CH$_2$—CH$_2$— or —CH$_2$—CH$_2$—CH$_2$—; as well as mixtures of two or more such derivatives.

In the case of compounds of formula I having a single chiral centre, racemic mixtures and mixtures enriched in one or other enantiomer, and the pure enantiomers, also form part of the invention.

In the case of compounds of formula I having more than one chiral centre, any mixture of diastereomeres and enantiomers also forms part of the present invention.

Alkyl substituents R may be e.g. methyl, ethyl, n-propyl, i-propyl, n-butyl, i-butyl, t-butyl, n-pentyl, n-hexyl, n-heptyl, n-octyl, n-nonyl, n-decyl, n-undecyl or n-dodecyl.

Alkenyl substituents R include e.g. ethenyl, n-propenyl, n-butenyl, n-pentenyl, n-hexenyl, n-octenyl, n-decenyl and n-dodecenyl.

Cycloalkyl substitutes R are e.g. cyclopentyl, cyclohexyl, cyclooctyl, cyclodecyl and cyclododecyl.

Aryl residues R are phenyl or naphthyl residues each of which is optionally substituted by e.g. $C_1$-$C_4$alkyl.

When R is aralkyl, it may be, for instance, benzyl, phenethyl or naphthylmethyl.

Alkylene residues X are e.g. methylene, ethylene, n-propylene, n-butylene, i-butylene, n-pentylene, n-hexylene, n-heptylene, n-octylene, n-decylene and n-dodecylene.

Alkenylene residues X include ethylene, n-propenylene, n-butenylene, n-pentenylene, n-hexenylene, n-octenylene, n-decenylene and n-dodecenylene.

Arylene residues X are phenylene or naphthylene each optionally substituted by e.g. $C_1$-$C_4$alkyl.

Preferred substituents R are $C_1$-$C_6$alkyl groups, in particular methyl. X is preferably a $C_1$-$C_6$alkylene residue, more preferably methylene or ethylene and, in particular, methylene.

Specific examples of compounds of formula I include:
3-hydroxy-3-phosphonobutanoic acid
3-hydroxy-3-phosphonopentanoic acid
3-hydroxy-3-phosphonohexanoic acid
3-hydroxy-4-methyl-3-phosphonopentanoic acid
3-hydroxy-3-phosphonoheptanoic acid
3-hydroxy-3-phosphonooctanoic acid
3-hydroxy-3-phosphonononanoic acid
3-hydroxy-3-phosphonodecanoic acid
3-hydroxy-3-phosphonoundecanoic acid
3-hydroxy-3-phosphonododecanoic acid
3-hydroxy-3-phosphonopentadecanoic acid
3-hydroxy-6-methyl-3-phosphonoheptanoic acid
4-hydroxy-4-phosphonopentanoic acid
4-hydroxy-4-phosphonohexanoic acid
4-hydroxy-5-methyl-4-phosphonohexanoic acid
4-hydroxy-4-phosphonoheptanoic acid
4-hydroxy-4-phosphonooctanoic acid
4-hydroxy-4-phosphonononanoic acid
4-hydroxy-4-phosphonodecanoic acid
4-hydroxy-4-phosphonoundecanoic acid
4-hydroxy-4-phosphonododecanoic acid
4-hydroxy-7-methyl-4-phosphonooctanoic acid
4-hydroxy-5-methyl-4-phosphonooctanoic acid
4-hydroxy-5-ethyl-4-phosphonooctanoic acid
4-hydroxy-7-methyl-4-phosphonononanoic acid
4-hydroxy-3-methyl-4-phosphonopentanoic acid
4-hydroxy-2-methyl-4-phosphonopentanoic acid
4-hydroxy-2-methyl-4-phosphonooctanoic acid
5-hydroxy-5-phosphonohexanoic acid
5-hydroxy-5-phosphonoheptanoic acid 5-hydroxy-5-phosphonooctanoic acid
5-hydroxy-5-phosphonononanoic acid
5-hydroxy-5-phosphonodecanoic acid
5-hydroxy-5-phosphonoundecanoic acid
5-hydroxy-5-phosphonododecanoic acid
6-hydroxy-6-phosphonoheptanoic acid
6-hydroxy-6-phosphonododecanoic acid
5-hydroxy-2-methyl-5-phosphonohexanoic acid
5-hydroxy-2-methyl-5-phosphonoheptanoic acid
12-hydroxy-12-phosphonotridecanoic acid
10-hydroxy-10-phosphonoeicosanoic acid
3-cyclohexyl-3-hydroxy-3-phosphonopropanoic acid
3-hydroxy-3-phenyl-3-phosphonopentanoic acid
3-hydroxy-4-phenyl-3-phosphonobutanoic acid
4-hydroxy-6-phenyl-4-phosphonohexanoic acid
3-hydroxy-3-phosphono-but-4-enoic acid
4-hydroxy-4-phosphonopent-2-enoic acid
2-(1-hydroxy-1-phosphonopentyl)benzoic acid
3-(1-hydroxy-1-phosphonopentyl)benzoic acid
4-(1-hydroxy-1-phosphonopentyl)benzoic acid
3-hydroxy-3-phosphonobutanoic acid trisodium salt
3-hydroxy-3-phosphonobutanoic acid ammonium salt
3-hydroxy-3-phosphonopentanoic acid triethyl ammonium salt
3-hydroxy-3-phosphonopentanoic acid dodecylamine salt.

The present invention also provides a first process for the production of a compound of formula I, comprising reacting a keto ester having the formula II:

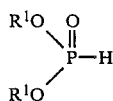

II in which R and X have their previous significance and $R^1$ is H or $C_1$-$C_6$alkyl, provided that $R^1$ is not H if X is methylene, with a phosphorus trihalide, preferably $PCl_3$, in the presence of water, or a carboxylic acid or carboxylic acid anhydride, preferably acetic acid or acetic anhydride, and subsequently adding water, if not already present.

The compound of formula I so obtained, often containing minor amounts of the corresponding dehydrated product, may be worked up by conventional methods.

In a second process according to the present invention a compound of formula I may be produced by reacting, in the presence of a catalyst e.g. an alkali metal fluoride, a dialkyl phosphite of formula III:

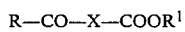

III in which $R^1$ has its previous significance, with a keto-ester of formula IV:

R—CO—X—COOR$^1$   IV in which R, X and $R^1$ have their previous significance, and the individual groups $R^1$ may be the same or different, to produce a compound having the formula V:

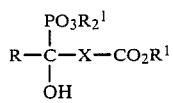

V and then hydrolysing the ester groups e.g. by heating compound of formula V under reflux conditions in the presence of mineral acid, to produce a free acid of formula I.

Again the reaction product, often containing minor amounts of the corresponding dehydrated product can be worked up by conventional methods.

In a third process according to the present invention, an intramolecular lactone derivative of a compound of formula I, in which X is —$CH_2CH_2$— or —$CH_2CH_2CH_2$— residue, may be produced by reacting a dialkyl phosphite of formula III, in the presence of sodium metal, with an alkyl ester of an acid having the formula VI:

R—CO—($CH_2$)$_n$—CO$_2$R$^1$   VI in which R and $R^1$ have their previous significance and n is 2 or 3 to produce an ester-lactone compound of formula VII or VIIA:

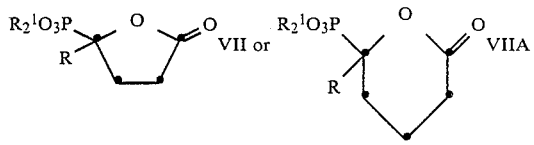

and then hydrolysing the ester groups, e.g. by heating the mixture under reflux conditions in the presence of a mineral acid, to give a lactone derivative having the formula VIII or VIIIA:

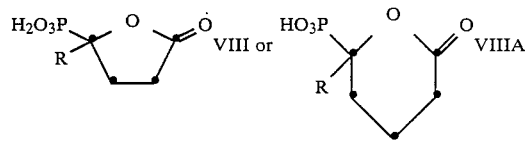

in which R has its previous significance.

The compounds of formula I, and their derivatives, have been found to have valuable properties in a wide variety of applications.

For example, the compounds of formula I have been shown to exhibit good corrosion- and/or scale inhibiting properties, good activity as anti-foulants in aqueous applicational media; and effective performance as sealing smut inhibitors in aqueous aluminium coating compositions.

They may also be used for pre-treatment of metal surfaces e.g. for cleaning purposes or as masking agents for ions that impair the activity of scale/corrosion inhibitors.

Accordingly, the present invention also provides a composition comprising an applicational medium and, as functional additive, at least one compound of formula I or a derivative thereof.

The applicational medium may be e.g. a wholly aqueous medium, a partly aqueous medium or a non-aqueous medium.

1. Use as corrosion- and/or scale inhibitor in wholly or partly aqueous additive applicational media The compound (or derivative) of formula I may be used alone, but may also be used in conjunction with other compounds known to be useful in the treatment of applicational media.

In the treatment of systems which are completely aqueous, such as cooling water systems, air-conditioning system, steam-generating systems, sea-water evaporator systems, hydrostatic cookers, and closed circuit heating or refrigerant systems, further corrosion inhibitors may be used such as, for example, water soluble zinc salts; phophates; polyphosphates; phosphonic acids and their salts, for example, hydroxyethyl-diphosphonic acid (HEDP), nitrilotris methylene phosphonic acid and methylamino dimethylene phosphonocarboxylic acids and their salts, for example, those described in German Offenlegungsschrift No. 2632774, hydroxyphosphonoacetic acid, 2-phosphonobutane-1,2,4-tricarboxylic acid (PBSAM) and those disclosed in GB No. 1572406; nitrates, for example sodium nitrate; nitrites e.g. sodium nitrite; molybdates e.g. sodium molybdate; tungstates; silicates e.g. sodium silicate; benzotriazole, bisbenzotriazole or copper deactivating benzotriazole or tolutriazole derivatives such as their Mannich base derivatives; N-acyl sarcosines; N-acylimino diacetic acids; ethanolamines; fatty amines; and polycarboxylic acids, for example, polymaleic acid and polyacrylic acid, as well as their respective alkali metal salts, copolymers of maleic anhydride, e.g. copolymers of maleic anhydrid and styrene sulfonate, copolymers of acrylic acid e.g. copolymers of acrylic acid and hydroxy-alkylated acrylic acid, and substituted derivatives of polymaleic and polyacrylic acids and their copolymers.

Particularly interesting mixtures are those of compounds of formula I with HEDP and/or PBSAM and/or benzotriazole or tolutriazole.

Moreover, in such completely aqueous systems, the compound of formula I may be used in conjunction with dispersing and/or threshold agents e.g. polymerised acrylic or methacrylic acid (or its salts) or acrylamide homo- and copolymers.

Further additives may be precipitating agents such as alkali metal orthophosphates, carbonates; oxygen scavengers such as alkali metal sulphites and hydrazines; sequestering agents such as nitrilotriacetic acid and its salts; antifoaming agents such as silicones e.g. polydimethylsiloxanes, distearylsebacamide, distearyl adipamide and related products derived from ethylene oxide and/or propylene oxide condensations, in addition to fatty alcohols, such as capryl alcohols and their ethylene oxide condensates; and biocides e.g. amines, quaternary ammonium compounds, chlorophenols, sulphur-containing compounds such as sulphones, methylene bis thiocyanates and carbamates, isothiazolones, brominated propionamides, triazines, phosphonium compounds, chlorine and chlorine-release agents and organometallic compounds such as tributyl tin oxide may be used.

If the aqueous applicational medium is not completely aqueous, e.g. if it is an aqueous machining fluid formulation or a hydraulic fluid, it may be e.g. a water dilutable cutting or grinding fluid.

The aqueous machining fluid formulations used as a component of the compositions according to the invention may be e.g. metal working formulations. By "metal working" we mean reaming, broaching, drawing, spinning, cutting, grinding, boring, milling, turning, sawing, non-cutting shaping, rolling or quenching.

Examples of water-dilutable cutting or grinding fluids into which the corrosion inhibiting compound of formula I may be incorporated include:

(a) Aqueous concentrates of one or more corrosion inhibitors, and optionally one or more anti-wear additives, used at dilutions of 1:50 or 1:100, which are usually employed as grinding fluids;

(b) Polyglycols containing biocides, corrosion inhibitors and anti-wear additives which are used at dilutions of 1:20 to 1:40 for cutting operations and 1:60 to 1:80 for grinding;

(c) Semi-synthetic cutting fluids similar to (b) but containing in addition 10 to 25% oil with sufficient emulsifier to render the water diluted product translucent;

(d) An emulsifiable mineral oil concentrate containing, for example, emulsifiers, corrosion inhibitors, extreme pressure/anti wear additives, biocides, antifoaming agents, coupling agents etc; they are generally diluted from 1:10 to 1:50 with water to a white opaque emulsion;

(e) A product similar to (d) containing less oil and more emulsifier which on dilution to the range 1:50 to 1:100 gives a translucent emulsion for cutting or grinding operations.

For those partly-aqueous systems in which the aqueous applicational medium is an aqueous machining fluid formulation or a hydraulic fluid the compound of formula I may be used singly, or preferably in admixture with other additives e.g. known further corrosion inhibitors or extreme-pressure additives.

Examples of other corrosion inhibitors which may be used in these aqueous systems, in addition to the compound of formula I include the following groups:

(a) Organic acids, their esters or ammonium, amine, alkanolamine and metal salts, for example, benzoic acid, p-tert-butyl benzoic acid, disodium sebacate, triethanolamine laurate, iso-nonaoic acid, triethanolamine salt of p-toluene sulphonamido caproic acid, triethanolamine salts of benzene sulphonamide caproic acid, triethanolamine salts of 5-ketocarboxylic acid derivatives as described in European Pat. No. 41927, sodium N-lauroyl sarcosinate or nonyl phenoxy acetic acid;

(b) Nitrogen containing materials such as the following types: fatty acid alkanolamides; imidazolines, for example, 1-hydroxyethyl-2-oleyl-imidazolines; oxazolines; triazoles for example, benzotriazoles; or their Mannich base derivatives; triethanolamines; fatty amines; inorganic salts, for example, sodium nitrate; and the carboxy-triazine compounds described in European Patent Application No. 46139;

(c) Phosphorus containing materials such as the following types: amine phosphates, phosphonic acids or inorganic salts, for example, sodium dihydrogen phosphate or zinc phosphate;

(d) Sulphur containing compounds such as the following types: sodium, calcium or barium petroleum sulphonates, or heterocyclics, for example, sodium mercaptobenzothiazole. Nitrogen containing materials, particularly triethanolamine, are preferred.

2. Use as antifoulants in aqueous applicational media

Compounds of formula I also function as dispersing agents and/or antifoulants towards common deposits, e.g. iron oxides and/or iron salts, calcium and magnesium deposits, e.g. their carbonates, sulphates, oxalates and phosphates, and silt, alumina, silicates and clays found in such waters.

In particular, the compounds of formula I disperse deposits in an aqueous system containing 5–1500 ppm by weight of calcium ion as well as suspended solids. This aspect of the present invention finds particular use in the china clay industry in which it is important to obtain slurries which will not appreciably separate out during transportation from the clay pits to the user. At high concentrations of suspended solids in these slurries, the compounds of formula I have been found to disperse china clay and to be of value as "in-process" dispersants and as grinding aids.

3. Use as sealing smut inhibitors during sealing of anodically-produced oxide layers on aluminium During such sealing, using hot or boiling water, not only are the pores of the oxide layers sealed, but a thick velvety coating (sealing smut) is also formed over the whole surface. The compounds of formula I are useful, in such applications, as sealing smut inhibitors.

The amount of the compound of formula I present in the composition of the invention will vary depending upon the function which the compound of formula I performs and on the composition of the applicational medium.

The compounds of formula I are used in less than stoichiometric proportions e.g. in amounts ranging from 0.1 to 50,000 ppm (0.00001 to 5% by weight) more preferably from 1 to 500 ppm (0.0001 to 0.05% by weight) based on the applicational medium.

The following Examples further illustrate the present invention.

Example 1: 3-Hydroxy-3-phosphonobutanoic acid

Ethyl acetoacetate (128 ml, 1 mole) is stirred at room temperature whilst phosphorus trichloride (92 ml, 1 mole) is added over 18 minutes. The mixture is then heated at 50° C. for 2 and half hours. After cooling to room temperature, glacial acetic acid (120 g, 2 moles) is added. After stirring at room temperature, the mixture is then heated to 70° C. and some volatile material distilled off. After 3 hours, 50 ml of water is cautiously added and the whole heated at reflux for 4 hours. After cooling, the solvents are removed in vacuo to give 173 g (94%) of a brown viscous oil, which by $^{31}P$ nmr is shown to be the title product contaminated with 15% of the corresponding dehydrated compound. Trituration with acetone gives the pure product as a white solid.

$^{31}P$ nmr: δ 24.1 tq.

$C_4H_9O_6P$ requires C 26.1%, H 4.9%, P 16.8%. found C 25.9%, H 5.15%, P 17.02%.

Example 2: 3-Hydroxy-3-phosphonobutanoic acid

Ethyl acetoacetate (0.2 moles) and diethylphosphite (0.2 moles) are stirred at room temperature with potassium fluoride (1 mole) for 6 hours. The product is extracted with dichloromethane and distilled to give 32% of 3-hydroxy-3-phosphonobutanoic acid triethyl ester (b.p. 114°–120° C./6.5 mm Hg) which gives the free acid (90%) on refluxing with 18% hydrochloric acid (200 ml) for 15 hours again containing 15% of the dehydrated product.

Example 3: 3-Hydroxy-3-phosphonopentanoic acid

Methyl propionyl acetate (0.5 moles) is stirred at room temperature whilst phosphorus trichloride (0.5 moles) is added over 10 minutes. After a further 10 minutes, acetic acid (1 mole) is added. The solution becomes heterogeneous for a time. After 7 hours at room temperature, the mixture is heated to 90° C. and some volatile material removed over 2 hours. The remaining mixture is then cooled to room temperature. 250 ml of water is added with an initial vigorous reaction and exotherm. When the addition is complete, the mixture is refluxed for 4 hours. The solvents are then removed under reduced pressure to give a brown viscous resin (yield 100%) which $^{31}P$ nmr spectroscopy shows to be a 3:1 mixture of 3-hydroxy-3-phosphonopentanoic acid and 3-phosphonopent-2-enoic acid.

$^{31}P$ nmr: δ 24.1 q 3-hydroxy-3-phosphonopentanoic acid; δ 13.2 dt 3-phosphonopent-2-enoic acid.

Example 4: 4-Hydroxy-4-phosphonopentanoic acid

Sodium sand (2 g) in dry toluene (750 ml) is stirred at room temperature and diethylphosphite (0.69 moles) is added. The mixture is heated for 1 hour at 80° C. until all sodium has dissolved. Ethyl levulinate (0.69 moles) is added over 20 minutes and the reaction heated at reflux for 9 hours. After cooling, the solvent is removed under reduced pressure. Distillation of the residue gives 28% of a diethyl ester-lactone product b.p. 130° C./3 mm Hg [lit. 100°–104° C./0.2 mm Hg].

$^{31}P$ nmr: δ 22.2 m.

Hydrolysis of this product, by refluxing in 300 ml 18% HCl for 10 hours, gives an almost quantitative yield of an intramolecular lactone of 4-hydroxy-4-phosphonopentanoic acid.

$^{31}P$ nmr: δ 18.6 m.

Example 5: 3-Hydroxy-3-phosphonotridecanoic acid

Methyl-3-ketotridecanoate (4 g) is stirred at room temperature and phosphorus trichloride (2.27 g) added. The mixture is then heated at 50° C. for 2.5 h before cooling and addition of glacial acetic acid (1.98 g). The system is then heated between 50° and 70° C. for 4 h and after cooling water (50 ml) is added causing an initially vigorous exotherm. After complete addition of water the two-phase system is heated at reflux for 12 h.

After cooling the product is extracted into ether, which is then dried and evaporated in vacuo to leave the product as a pale yellow oil (3.9 g), contaminated with 16% of the corresponding α, β unsaturated carboxylic acid.

$^{31}P$ nmr: δ 25.9 ppm 3-hydroxy-3-phosphonotridecanoic acid; δ 14.1 ppm 3-phosphonotridec-2-enoic acid.

Example 6

The n-hydroxy-n-phosphonocarboxylic acids prepared have been tested as a corrosion inhibitor for ferrous metals in a recirculating cooling water rig using different water compositions. The test system and results for 2-hydroxy-2-phosphonobutanoic acid (containing 15% of the dehydrate material—as obtained in Example 1) are described below:

The recirculating rigs consist of a 20 l reservoir of test water which is recirculated over precleaned, preweighed mild steel heat exchangers and coupons. The reservoir temperature is kept at 40° C. and a high level inhibitor treatment maintained for 24 hours before continuing with maintenance level for a further 6 days. The heat exchanger and coupons are then cleaned and the corrosion rate determined. The results obtained are summarised in the following table II:

TABLE

| Water | | Corrosion Rate (mls per year) | | |
|---|---|---|---|---|
| | | Heater 1 | Heater 2 | Coupons |
| 1 M | blank | 84.2 | 87.1 | 52.3 |
| | with additive | 6.1 | 8.9 | 4.5 |
| 2 M | blank | 106.4 | 107.0 | 73.3 |
| | with additive | 4.4 | 4.4 | 3.6 |
| 5 M | blank | 23.4 | 27.0 | 19.2 |
| | with additive | 1.39 | 0.99 | 0.4 |
| 8 M | blank | 10.7 | 10.5 | 7.5 |
| | with additive | 1.98 | 2.97 | 1.95 |

The water analyses at thje start of the test are

| | pH | PA ppm as $CaCO_3$ | TA ppm as $CaCO_3$ | TH ppm as $CaCO_3$ | CaH ppm as $CaCO_3$ | Cl ppm as $Cl^-$ | $SO_4$ ppm as $SO_4^2$ | Ryznar index at 40° |
|---|---|---|---|---|---|---|---|---|
| 1M | 7.6 | 0 | 20 | 10 | 10 | 10 | <5 | 10.8 |
| 2M | 7.2 | 0 | 20 | 110 | 75 | 5 | 110 | 9.4 |
| 5M | 7.6 | 0 | 204 | 216 | 150 | 36 | 40 | 6.4 |
| 8M | 8.0 | 0 | 210 | 580 | 500 | 300 | 40 | 5.2 |

In this Table
PA = phenol alkalinity
TA = total alkalinity
TH = total hardness
CaH = calcium hardness For the corrosion tests in 5M and 8M water on the recirculating rig system 2 ppm of hydroxyethyl diphosphonic acid (HEDP) is added as a scale control agent.

For the results quoted, the initial high dose level is 80 ppm of active ingredient which is reduced to 20 ppm during the maintenance period. In all cases 4 ppm of tolutriazole (TTA) is added during the high dose passivation period, being reduced to 1 ppm during maintenance to protect yellow metals present.

Example 7

A 100 ml aqueous solution containing 200 ppm $Ca^{2+}$ (as $CaCO_3$), 100 ppm $HCO_3^-$ (as $CaCO_3$), 100 ppm $Fe^{2+}$ and x ppm of the additive under test maintained at 50° C. for 1 hour. After measuring the turbidity, the amount of iron present in the filtrate after filtration through either a 0.22 μm filter or a 0.30 μm filter is recorded on a scale of 0 (bad)–10 (good). The results shown below in Table II were obtained using, as test compound, 3-hydroxy-3-phosphonobutanoic acid, as obtained in Example 1.

TABLE II

| x (ppm additive) | Turbidity (NTU) | Iron Present | |
|---|---|---|---|
| | | 0.22 μm | 3.0 μm |
| 0 [blank] | 40 | 0 | 0 |
| 10 | 1 | 9.4 | 9.2 |
| 8.5 | 0.9 | 9.3 | 9.5 |
| 6.75 | 1.3 | 9.6 | 9.8 |

NTU denotes Nepholometric Turbidity Units

We claim:
1. Compounds having the formula I:

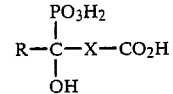

I wherein R is a $C_1-C_{12}$ straight or branched chain alkyl residue, a $C_2-C_{12}$ straight or branched chain alkenyl residue, a $C_5-C_{12}$ cycloalkyl residue, a $C_6-C_{10}$ aryl residue or a $C_7-C_{12}$ aralkyl residue; and X is a $C_1-C_{10}$ straight or branched alkylene residue, a $C_2-C_{10}$ straight or branched chain alkenylene residue or a $C_6-C_{10}$ arylene residue; as well as derivatives of the compounds of formula I; and enantiomers, racemic mixtures, and mixtures of diastereomers.

2. Compounds according to claim 1 in which R is $C_1-C_6$ alkyl and X is $C_1-C_6$ alkylene.

3. Compounds according to claim 2 in which R is methyl and X is ethylene or methylene.

4. Compounds according to claim 3 in which X is methylene.

* * * * *